United States Patent [19]

Wilson et al.

[11] Patent Number: 5,621,172

[45] Date of Patent: Apr. 15, 1997

[54] METHOD AND APPARATUS FOR TESTING MATERIAL STRENGTHS

[75] Inventors: James B. Wilson; Milo L. Clauson, both of Corvallis, Oreg.

[73] Assignee: State of Oregon Acting by and through the State Board of Higher Education on Behalf of Oregon State University, Eugene, Oreg.

[21] Appl. No.: 415,500

[22] Filed: Apr. 3, 1995

[51] Int. Cl.$^6$ ................................................. G01N 29/20
[52] U.S. Cl. ................................................ 73/579; 73/602
[58] Field of Search ............................... 73/579, 599, 600, 73/602; 364/508

[56] References Cited

U.S. PATENT DOCUMENTS

| | | | |
|---|---|---|---|
| 3,513,690 | 5/1970 | Pellerin et al. | 73/594 |
| 3,531,983 | 10/1970 | Heath et al. | 73/579 |
| 3,877,294 | 4/1975 | Shaw | 73/579 |
| 4,059,988 | 11/1977 | Shaw | 73/579 |
| 4,061,017 | 12/1977 | Sloane et al. | 73/579 |
| 4,399,701 | 8/1983 | Dunlop | 73/579 |
| 4,502,329 | 3/1985 | Fukunaga et al. | 73/579 |
| 4,689,993 | 9/1987 | Slettemoen | 73/579 |
| 4,702,111 | 10/1987 | Holland | 73/579 |
| 4,838,085 | 6/1989 | Pellerin et al. | 73/597 |
| 4,858,469 | 8/1989 | Hosgood et al. | 73/579 |
| 4,926,691 | 5/1990 | Franklin et al. | 73/579 |
| 5,024,091 | 6/1991 | Pellerin et al. | 73/597 |
| 5,165,270 | 11/1992 | Sansalone et al. | 73/12.08 |
| 5,419,197 | 5/1995 | Oai et al. | 73/659 |

*Primary Examiner*—John E. Chapman
*Attorney, Agent, or Firm*—Klarquist Sparkman Campbell Leigh & Whinston, LLP

[57] ABSTRACT

An apparatus and a non-destructive method for evaluating material strengths is described. One embodiment of the apparatus comprises a waveform generator that generates either (1) a sinusoidal waveform having a frequency that sweeps from a low frequency to a high frequency, or a high frequency to a low frequency, wherein the low frequency is from about 10 Hz to about 150 Hz, and the high frequency is from about 6,000 Hz to about 24,000 Hz, or (2) a pseudo random within the frequency range of from about 150 Hz to about 6,000 Hz. An electromechanical driver is electronically linked to the waveform generator and mechanically coupled to a test material, particularly in-service utility poles, at a drive position. Force and acceleration sensors are coupled to the test material at various positions. A microprocessor is used to collect digitized data from the force sensor and the accelerometers, perform a transfer function and determine the strength remaining in the test material using a neural network model.

31 Claims, 3 Drawing Sheets

METHOD AND APPARATUS FOR TESTING MATERIAL STRENGTHS

FIELD OF THE INVENTION

This invention concerns a method and apparatus for predicting the strength of materials, particularly the strength of wooden articles.

BACKGROUND OF THE INVENTION

There are only a few devices and methods known for non-destructively predicting the strength of a material. There is, however, a need for such devices. A device and method useful for determining the strength remaining in a wooden article, such as an in-service utility pole, is a prime example. There are about one hundred and sixty million wooden utility poles in service. Many states require that utility poles be inspected at least as often as every ten years, and replaced when the strength of the pole drops to below about two-thirds of its design load value. This is an onerous, if not impossible, time-consuming task. This is because determining the strength remaining in utility poles cannot be based solely on a visual inspection, regardless of whether the factors that diminish strength can be seen or not (eg., decay, checks, splits, etc.). Currently, the strength remaining in a utility pole cannot be determined unless the pole is actually broken, which defeats the purpose for the test. A method for testing the strength remaining in wooden articles, without ruining the article, is therefore needed.

Testing methods that do not break the test material but reduce the structural qualities thereof also are disfavored. Certain known techniques do reduce structural integrity. One example of such a method is boring a sample from the pole for inspection. Sample boring promotes fungal deterioration of the wood.

Non-destructive methods have been developed for testing the strength or quality of a material. These methods include X-ray, sonic, electrical resistance, boring and hammering. One disadvantage of most of these methods is that they do not predict strength, but rather require subjective evaluation of the results obtained by the analytical method utilized. For instance, X-ray equipment provides a mass profile that must be adjusted for the circular cross-section of the pole to determine its density. The inspector then must subjectively interpret this profile to ascertain the condition of the pole. At best, the X-ray method may identify void spaces due to decay. Moreover, according to U.S. Pat. No. 4,059,988, which is incorporated herein by reference, X-ray analysis is slow, and therefore is not practical for field use. As a result, X-ray analysis is seldom, if ever, used. And, there currently are no known X-ray methods for predicting the strength remaining in utility poles.

Sonic energy also has been used in attempts to ascertain the strength remaining in wooden poles. The theory underlying the relationship between strength and vibrational attenuation is not entirely understood. However, wooden structures apparently exhibit both wide band attenuation of vibratory energy and selective attenuation within narrow frequency ranges. In general, within the frequency range of about 10–24,000 Hz, the degree of attenuation (acoustic impedance) is related to the strength of the material. More specifically, strength is inversely related to attenuation. Greater attenuation is apparent at higher frequencies. In other words, good wood presents a lower acoustic impedance to low frequencies than to high frequencies. Sonic testing is quick and is therefore more suitable for an initial screening of a wooden article than X-ray procedures.

There are several examples of patented devices that use sonic energy for testing wooden materials. U.S. Pat. No. 3,877,294 describes a device that uses a vibration head to inject a tunable single frequency into a pole at a predetermined point. The vibrational energy is then detected at different points along the pole by a transducer. Comparisons are made between the energy emerging at certain reference points directly opposite the injection point, and energy emerging at other points to determine whether there are voids or regions of rot in the pole.

Another example of a patented device that utilizes sonic energy is U.S. Pat. No. 3,531,983. This device generates an acoustic wave by striking an article with a hammer, which is a method common to a number of known inventions. This procedure does not allow an operator to select the frequency of sound waves that are applied to the wooden article.

In summary, there are a number of techniques that have been developed ostensibly for the determination of material strength. The primary deficiency of all of these devices is the low correlation between predicted and actual strength. Moreover, most known devices do not predict strength, but rather provide some empirical information, such as the time of sonic wave propagation. The interpretation of the output is left to the operator.

SUMMARY OF THE INVENTION

A new apparatus and method for evaluating material strength have now been invented. These overcome many of the disadvantages of known devices and provide a better predictive accuracy. This appears to result from at least one of: (1) the method of generating and transmitting the waveform into the test material; (2) the use of a transfer function; and (3) a more sophisticated analysis method. The present invention also provides an actual prediction of the strength remaining in the test material in terms of the modulus of rupture (MOR). This step is not left to the interpretation of the operator as with most known devices. Moreover, the correlation between actual material strength and that predicated by the present invention is significantly superior to known apparatuses and methods.

One embodiment of the invention comprises a waveform generator, typically a digital waveform generator. The waveform generator generates either a sinusoidal waveform, or a pseudo random waveform having a uniform power distribution over a specified frequency range, such as from about 150 Hz to about 6,000 Hz. The frequency of the sinusoidal waveform is purposefully varied, i.e., the frequency range is swept over a finite time period. The frequency may be swept from a low frequency to a high frequency, or a high frequency to a low frequency, i.e., the method works whether the frequency scan is from low to high frequencies, or from high to low frequencies. The low frequency generally is from about 10 Hz to about 150 Hz, and the high frequency is from about 6,000 Hz to 24,000 Hz. The frequency preferably is swept from a low frequency of about 150 Hz to a high frequency of about 6,000 Hz, or from about 6,000 Hz to about 150 Hz.

A driver, which is electronically linked to the waveform generator, is used to transmit the waveform into the test material. The driver generates a localized, nonpermanent deformation in the test material, which causes the material to vibrate. The driver may be any suitable driver, including without limitation, an electromechanical driver, a piezoceramic driver and an electromechanical/piezo-ceramic driver. The driver generally includes four major components: (1) the force generator; (2) a force sensor; (3) an accelerometer; and (4) a connector for coupling the driver to the material to be tested.

The driver is coupled to the test material at a position referred to herein as the "drive point" or "drive position" using a fastener. The drive point should be chosen to optimize the results obtained with the device. The optimum drive point varies depending upon the particular material being tested, and its three dimensional shape. For circular cross-section utility poles, the drive point generally is at or adjacent to the groundline, and preferably is at or less than about six inches above groundline. However, it should be understood that the device will work even if the drive point is other than at or adjacent to the groundline.

In one embodiment, the force sensor and first accelerometer are integral with the driver and are coupled to the test material. The apparatus also may include additional accelerometers that are coupled to the test material. More specifically and with reference to cylindrical, elongated utility poles as an example, the first accelerometer is attached on the exterior surface of the pole at the drive point. The optional additional accelerometers may be attached to the test material at various locations. In general, the second accelerometer is coupled to the material at a position substantially diametrically opposed to the drive point. Any additional accelerometers generally are coupled to the material on the same side of the material as the drive point, and spaced therefrom. This spacing distance for positioning the optional accelerometers may vary; however, a currently preferred distance for testing in-service utility poles is less than about 24 inches, and preferably is from about 4 inches to about 24 inches from the drive point as measured along the surface of the object being tested.

As stated above, the driver generally is mechanically fastened to the test material. This also is true for the accelerometers. For instance, both the driver and accelerometer(s) can be attached to utility poles using mechanical fasteners, such as tapered screws having a length of from about 1 inch to about 1.5 inches.

The analog information received by the force sensor and accelerometer(s) is converted into digital information. The digital data is relayed to and processed by a microprocessor. As with any electronic device, a power source is provided to supply electrical power to the electronic components.

A frequency domain transfer computation is performed by the processor. The transfer function is performed on the force input data, and on the one or more response functions provided by the one or more accelerometers. The transfer function is then input into a neural network model. The neural network model is used to predict either the modulus of rupture (MOR), strength of the material, or the quality of the material being tested.

A preferred embodiment of the apparatus is a manually transportable (i.e., the device can be carried by a single individual without the aid of additional lifting equipment) device that is useful for the non-destructive evaluation of material strength in a wooden article, particularly in-service utility poles. The device includes a waveform generator for generating either (1) a sinusoidal waveform that sweeps from a low frequency to a high frequency, or a high frequency to a low frequency, over the frequency ranges stated above, or (2) a pseudo random waveform through the frequency range as wide as from about 150 Hz to about 6,000 Hz. The waveform generator is electronically linked to a driver as stated above, wherein the driver is selected from the group consisting of electromechanical drivers, piezo-ceramic drivers and electromechanical/piezo-ceramic drivers. Moreover, a force sensor, a first or primary accelerometer, and perhaps additional accelerometers, are coupled to the pole in the manner and in the positions described above. The driver transmits the waveform into the utility pole. A microprocessor samples analog information and produces digital records concerning the information received from the force sensor and the accelerometer(s). Transfer functions are then computed from the force and accelerometer records.

One embodiment of the invention is a method for testing the remaining strength of a material. The method comprises transmitting into a material at a drive point either a sinusoidal waveform that sweeps from a low frequency to a high frequency, or a high frequency to a low frequency, wherein the low frequency is from about 10 Hz to about 150 Hz, and the high frequency is from about 6,000 Hz to about 24,000 Hz, or a pseudo random waveform within the frequency range of from about 150 Hz to about 6,000 Hz. The force transmitted into the test material is measured using a force sensor at or substantially adjacent to the drive point. The attenuation of the waveform in the material also is determined using at least a first accelerometer that is coupled to the material at or adjacent to the drive point. A transfer function is performed on the inputs from the force sensor and accelerometer(s), and a neural network model is then used to predict the strength remaining in the material. The method may involve transmitting the waveform into the test material a plurality of times, wherein the frequency sweep time is less than about 2 seconds. Sweep time is not a critical feature of the invention, and may depend on certain controllable factors, such as the frequency range being swept. The correlation ($R^2$) between predicted remaining strength and actual remaining strength of the wooden articles is at least twice as good as the correlations of certain known techniques, and therefore provides a significant advantage over known methods.

DETAILED DESCRIPTION OF THE PREFERRED EMBODIMENTS

Devices and methods of the present invention are useful for determining the strength remaining in an article. The present invention provides a significant improvement over known techniques because the correlation between actual remaining strength and predicted strength is at least as high as about $R^2=0.7$. As discussed below, this correlation is significantly greater than with certain known devices, which have a typical correlation between actual remaining strength and predicted strength of less than about 0.36.

Without limiting the invention to one theory of operation, it currently is believed that the material strength properties of an article determines its vibration response to a force wave, such as a sound wave. As the strength of a material changes its vibration response also changes. The method of the present invention can be used to test material strengths on any material wherein the vibration response of the material changes as its strength changes. As a result, the invention can be used to test a variety of materials. A currently preferred embodiment of the invention has been developed for testing wooden articles. Examples of wooden articles that can be tested with the device, without limitation, include utility poles, timbers, laminated beams, pilings and wood-based composites.

I. DESCRIPTION OF ILLUSTRATED APPARATUS

Figure 1:
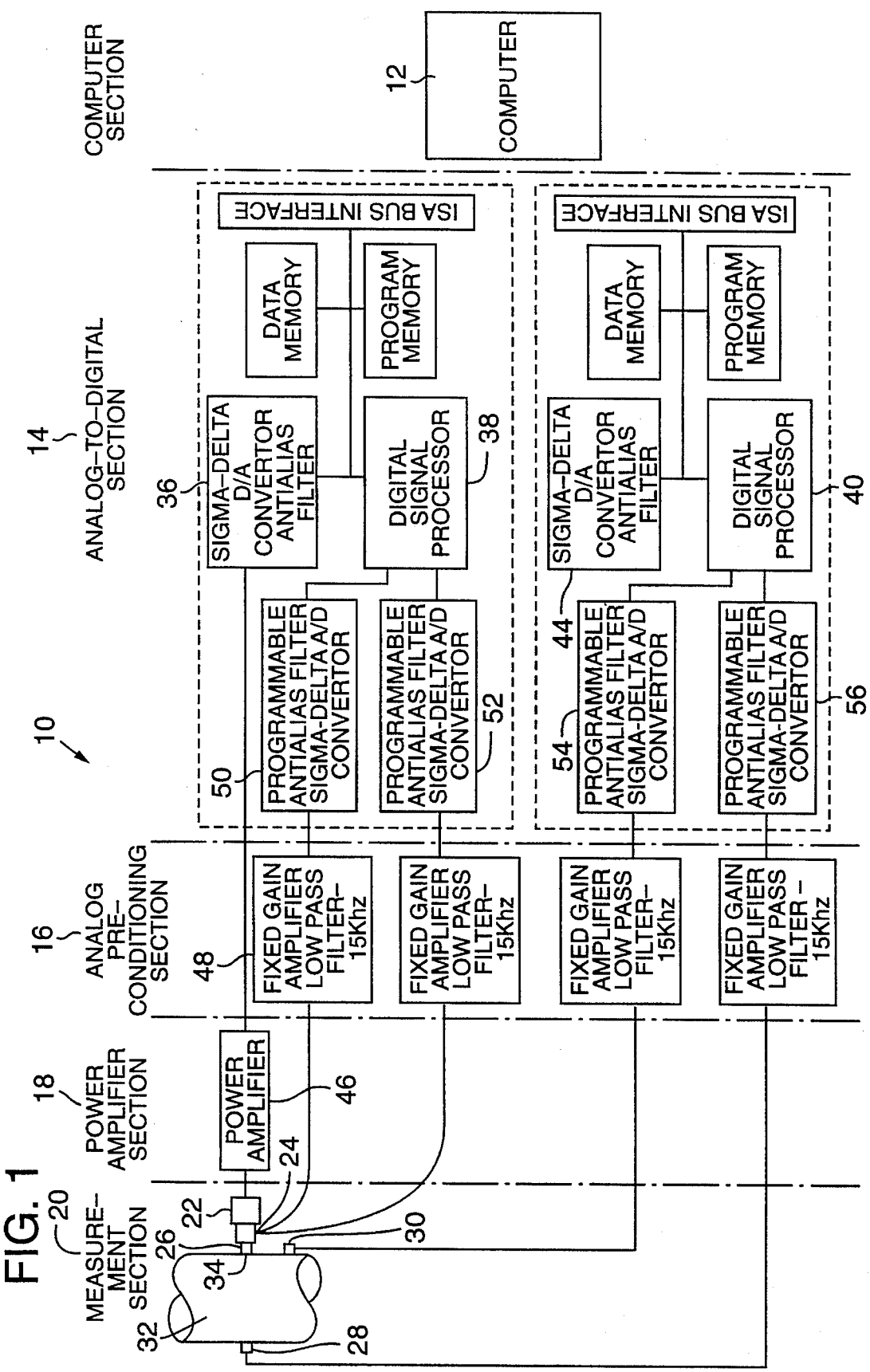
FIG. 1 is a block diagram illustrating certain features of one embodiment of the present invention.

As illustrated in FIG. 1, one embodiment of an apparatus according to the present invention can be artificially grouped in sections to illustrate the basic functions of the device. The first such section of device 10 is a computer section that utilizes a processor 12. One example of a suitable computer, without limitation, is an IBM personal computer. The computer section has several functions, including generating either a sinusoidal or a pseudo random waveform, sweeping the frequency of the waveform and receiving and collecting data.

The illustrated device 10 also includes a section 14 for converting the digital waveform into an analog signal, and for converting the analog data collected into a digital signal. An analog preconditioning section 16 is provided to amplify and filter the electronic signals that are relayed to analog-to-digital converters 50, 52, 54 and 56 from the computer 12. A power amplifier section 18 provides additional amplification of the electronic signal. Finally, a measurement section 20 is provided that includes a driver 22, a force sensor 24, and a primary or first acceleration sensor (also referred to as an accelerometer) 26. Generally, plural secondary acceleration sensors, such as sensors 28 and 30, also are provided in measurement section 20.

Figure 2:
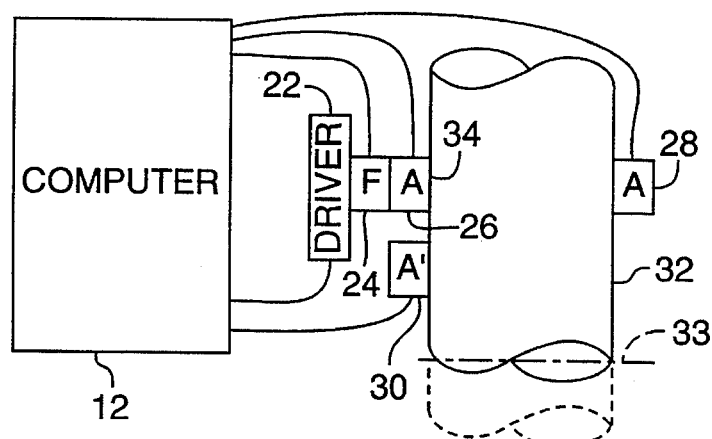
FIG. 2 is a schematic drawing illustrating certain structural features of one embodiment of the present invention.

As shown in FIG. 2, a first accelerometer 26 is mechanically coupled to the material to be tested, such as an in-service utility pole 32, at a drive position 34. For in-service utility poles, the drive position preferably is at or near groundline 33, and the second positions are adjacent thereto, preferably within from about 6 to about 24 inches away from the drive point. Computer 12 generates waveforms, preferably a sinusoidal swept frequency waveform, that are applied to the test material by the driver 22. The energy applied to pole 32 by driver 22 is detected by the force sensor 24 and accelerometers 26, 28 and 30. The accelerometers 26, 28 and 30 output analog data that is digitized, collected and stored by computer 12. The digitized data reflects the response of the material to the vibrational energy in terms of force and acceleration. Computer 12 then performs a transfer function analysis on the digitized data based on the force and acceleration data collected. A neural network model is then used to predict the strength and the quality of the pole based on this transfer function.

The output of device 10 can be in any desired format. Currently, the output preferably is presented in terms of the modulus of rupture (MOR), strength of the material tested, e.g., pole strength, and material classification. Alternatively, the pole quality may be presented in terms of a subjective rating system, such as an A, B, C or D rating system. With utility poles, the MOR preferably is calculated at groundline and assumes that the utility pole has a solid cross section.

Each of the individual components of the device, the interconnection of the components, and how to use the device are discussed below in more detail.

A. SWEPT WAVE FREQUENCY GENERATOR

An important aspect of the present invention is the generation of a reproducibly uniform and tunable force output vibrational energy that can be transmitted into the test material.

1. Digitally Synthesized Waveforms

A swept frequency sinusoidal waveform is generated to drive the driver 22. A swept frequency sinusoidal waveform can be generated in a number of ways, including both analog and digital generation. By way of example, an analog generator could use a voltage controlled frequency oscillator. For purposes of the present invention, the waveform preferably is synthesized digitally. Applying digitally synthesized swept frequency sinusoidal waveforms to a test material using the computer generator 12 allows a detailed measurement of the resonance and attenuation characteristics of the material being tested.

One embodiment of the present system uses a generator that can generate a maximum frequency range of from about 10 to about 24,000 Hz. A field test system also has been developed that uses a portable processor, such as a portable IBM personal computer, that can generate a frequency range of from about 10 Hz to about 10,000 Hz, preferably from about 150 Hz to about 6,000 Hz. The signal produced by the generator 12 has a uniform amplitude linear phase sine wave with a peak-to-peak magnitude of about 1.0 volt.

The sweep time for the frequency range typically is on the order of about one to two seconds, preferably about 1.5 seconds. The sweep time generally depends upon the range of frequencies that are swept. Furthermore, the present invention typically does not sweep the frequencies once, but preferably sweeps the frequencies a plurality of times.

There are alternative waveforms that will suffice. For instance, an alternative embodiment of the invention uses a pseudo random waveform which, when examined in the frequency domain, has a uniform frequency composition from about 150 Hz to about 6,000 Hz. "Pseudo random" as used herein means that the frequency range need not be swept from low frequencies to high frequencies, nor that the frequency be swept from high frequencies to low frequencies. The method will work regardless of the order in which the frequencies are transmitted to the test material.

2. Computer

The raw waveform data collected by the device 10 is stored and analyzed by computer 12. The general criteria for selecting the computer 12 therefore generally are as follows: (1) generation of the waveform, particularly sinusoidal swept frequency waveforms; (2) storage of the raw waveform data; (3) providing data reduction and parameter prediction from the neural network model; and (4) providing visual examination of all intermediate data processing. Virtually any personal computer likely will work for this invention. Currently, an IBM class personal computer with an Intel 386 or 486 microprocessor is suitable.

The field systems preferably will use a portable, battery-powered dedicated microprocessor. The portable personal computer will have one or more ISA bus cards inserted into it to provide the digitally synthesized waveform as well as the analog-to-digital components for measuring all response signals.

3. Digital-To-Analog Converter

The waveform generated by the computer 12 of FIG. 1 must be converted to an analog signal using a digital-to-analog convertor (D/A) 36. This can be done using conventional equipment. One example, without limitation, of a D/A converter 36 useful for the present invention is a 16 bit sigma-delta D/A converter with a programmable anti-alias output filter. The digital-to-analog converter 36 typically operates under the control provided by digital signal processor integrated circuit chips 38, 40.

Apparatus 10, particularly for the field trial apparatus, can use anti-alias filters, such as anti-alias filters 42, 44, to remove noise of particular frequencies. For instance, with a field testing device that sweeps up to frequencies of about 6,000 Hz, a filter can be used to remove noise above about 6,000 Hz. The anti-alias filters 42, 44 are used to smooth the discrete steps of the digital output waveform. Filters can be used in combination with the apparatus to apply sonic energy of specific frequencies to the material to be tested.

4. Swept Waveform Signal Input Amplifier

The analog signal from digital-to-analog convertor 36 is amplified by power amplifier 46 to energize the driver 22, which is mechanically attached to the material to be tested. One embodiment of an amplifier 46 used for this invention had a gain which was selectable from about zero to about twenty. Moreover, the amplifier 46, plus an impedance matching and step-up transformer (not shown), provided approximately 200 volts per volt of synthesized waveform. The power output from the amplifier 46 was about seven watts, although it is likely that this power output could be reduced to about 2 watts using additional conventional equipment. As a result, it currently is believed that the power output from the power amplifier 46 may range from about 2 to about 1 0 watts and still function correctly. A currently preferred power output is about 7 watts.

B. DRIVERS FOR APPLYING OSCILLATED FORCE TO MATERIAL

The amplified analog signal from the digital-to-analog converter 36 is input to driver 22. Driver 22 applies (also referred to as injects, injecting, transmits or transmitting) the synthesized waveform to the material to be tested. The driver 22 may be any useful driver now known or hereinafter developed, including an electromechanical driver, a piezoceramic driver and a electromagnetic/piezo ceramic driver. Driver 22 can be a conventional piece of equipment. One example of a commercially available driver 22 useful for the present invention is a Wilcoxon Model F4/F7 dual-drive electromagnetic and piezo-ceramic oscillator. This oscillator generates a ten-pound force to the test material over a frequency range of from about 30 Hz to about 12,000 Hz. A second example of a driver 22 useful for the present invention is a Wilcoxon Model F3 oscillator. This driver uses only an electromagnetic oscillator, rather than the combination of an electromagnetic and a piezo-ceramic oscillator. The Wilcoxon Model F3 oscillator generates about one pound of force over a frequency range of from about 200 Hz to about 5,000 Hz. This second Wilcoxon Model F3 likely is more useful in a manually transportable embodiment of the device.

Once a suitable driver 22 is selected, it is then mechanically coupled to the test material. Any conventional means now known or hereinafter developed for coupling the driver 20 to the test material can be used to practice the present invention. For instance, one method for mechanically coupling the driver 22 to a test material is to use a fastener, such as a wood screw.

C. FORCE SENSORS AND ACCELEROMETERS

Plural sensors are coupled to the test material to monitor the propagation of the waveform through the test material. More specifically, at least one force sensor 24 and at least one primary accelerometer 26 are used to monitor the response of the test material to the applied waveform. Plural secondary accelerometers 28 and 30 also can be used. The sensors provide a time history of the applied force and resulting acceleration. Typically, two or more waveform data sets are generated to test the material. If plural accelerometers are used, then accelerometers such as 26, 28 and 30 may be attached at separate locations along the test material. These sensors typically have a flat frequency response from less than about 150 Hz to greater than about 6,500 Hz. The response of the force sensor 24 preferably is less than about 1 lb-F/volt sensed. The acceleration response of accelerometers 26, 28 and 30 preferably should be less than about 1 g/volt sensed.

The Wilcoxon drivers discussed above by way of examples had the force sensor 24 and accelerometer sensor 26 attached thereto. The force sensor 24 has a response of about 9.1 lb-F/volt, and accelerometer 26 had a response of about 83 g/volt. Accelerometers 28 and 30 had a response of about 1 g/volt. A Wilcoxon F4/F7 driver had a useable force output of from about 10 Hz to about 14,000 Hz.

As shown in FIG. 2, the acceleration response sensors 26, 28 and 30 are coupled to the material to be tested to record the change in signal level between the drive point and the location where each sensor is mounted. The location of the secondary sensor 30 generally is about 6 inches from the drive point 34 of the driver 22 as measured along the surface of the object being tested. Sensor 26 preferably is coupled to the material at or adjacent to the drive point. Sensor 28 typically is coupled to the test material at a location directly opposite to the location of the driver 22 and drive point 34. For instance, on a utility pole 32 having a circular cross-section with a driver 22 mounted thereto as illustrated in FIG. 2, at least one secondary acceleration sensor 28 is attached to the back side of the pole in a position substantially diametrically opposed to the drive position 34. The position of sensor 28 need not be exactly diametrically opposed.

The frequency range for the secondary acceleration sensors 28 and 30 is from about 10 Hz through greater than about 7,000 Hz. The sensitivity of the secondary acceleration sensors 28 and 30 is flat over this frequency range. A signal sensitivity of the devices used during field testing was 1 g/volt acceleration sensed.

The accelerometers 26, 28 and 30 preferably have a rugged construction for field use. The accelerometers 26, 28 and 30 also preferably are hermetically sealed to prevent water damage to the sensitive electronic device. Without limitation, an example of an accelerometer, such as illustrated as sensor 28, known to be useful for the present invention is a Kistler Model 8612B5 accelerometer. A second example of a suitable secondary acceleration sensor is Kistler Model 8702B25.

D. ANALOG-TO-DIGITAL CONVERTER TO RECORD A DIGITIZED RESPONSE SIGNAL

The analog input signals from the force sensor 24 and plural acceleration sensors 26, 28 and 30 typically are amplified using conventional equipment. For instance, the analog signals from both the force sensor 24 and plural acceleration sensors 26, 28 and 30 may be amplified using a fixed gain amplifier 48. One example, without limitation, of an amplifier 48 useful for the present invention is a Kistler Model 5122. The amplifier 48 also generally includes a low-pass filter, such as a 15,000 Hz low-pass filter.

The amplified analog signals from amplifier 48 are then converted to digital signals using high speed A/D converters 50, 52, 54 and 56. One example of an A/D system containing converters 50, 52, 54 and 56 known to be useful for practicing the present invention is an Analogic Model D6000. The digital data emerging from the analog-to-digital converters 50, 52, 54 and 56 is then downloaded to a computer 12 for long term storage.

The invention may be modified from that stated above for use in a field testing situation. This is primarily due to the requirements that the field testing device be readily transportable, and preferably manually transportable. For portable devices according to the present system, fixed gain amplifiers likely will be more practical for use in conjunction with each sensor channel. The analog signals from the sensors 24, 26, 28 and 30 are thus input into individual analog-to-digital converters 50, 52, 54 and 56 as illustrated in FIG. 1. Each of the analog-to-digital converters 50, 52, 54 and 56 typically includes a digitally programmable anti-alias prefilter. Prefilters help minimize measurement errors from noise from components wherein the noise is greater than the upper test frequency used in the field test devices, such as greater than about 6,000 Hz. The analog-to-digital converters 50, 52, 54 and 56 preferably are controlled by digital signal processing integrated circuit chips which are in turn controlled by software in the computer.

In summary, a device 10 useful for field testing generally will use a general purpose IBM personal class computer 12 to generate a digital waveform that preferably is a swept frequency sinusoidal wave. This digital waveform is then converted into an analog signal, such as by using two general purpose analog signal processing cards, illustrated as section 14 in FIG. 1, which utilize digital signal processors 40 and 42. The synthesized analog output signal is then amplified using an external power amplifier 46 which is connected to the electromagnetic driver 22.

Analog response signals produced by the force sensor 24 and the accelerometers 26, 28 and 30, are amplified and conditioned by the signal conditioning unit 16. Conditioned analog signals from conditioning section 16 are then converted to a 16-bit digital form by the signal processing cards of section 14 as controlled by computer code within the digital signal processors 38 and 40. The digital signals are then transferred into the main computer 12 using specialized computer code which produces an estimate of the strength of the material being tested. Computer 12 also is useful for storing additional information, such as pole number, pole location, species, class, treatment type, condition, quality and strength.

It currently is believed that the best embodiment of the material testing device 10 will contain the features of the device 10 described above. However, alterations can be made to achieve reduced costs, lower power consumption, rugged construction and ease of transport. Such a unit likely would contain a general purpose microprocessor. The microprocessor would service high level activities such as user interface and top level data reduction functions. It also is likely that one or two specialized digital signal processors would be used to synthesize the output waveform and control the collection of the resultant response waveform. The commercial embodiment of this invention could incorporate many different computer integrated circuits and analog signal processing hardware, and still function substantially as described herein.

Moreover, it also should be noted that while a swept frequency waveform currently is preferred, other waveforms also may work to provide the necessary response functions that enable the device to extract strength estimates. The field prototype instrument incorporates both the swept sinusoid waveform as well as a pseudo random waveform. This alternative embodiment generates a waveform which, when examined in the frequency domain, has a uniform frequency composition from about 10 Hz to about 6,000 Hz. This response is essentially identical to the swept sinusoid in the magnitude component of the frequency domain; however, the waveforms are unique in the time domain.

E. SOFTWARE FUNCTIONS

Figure 3:
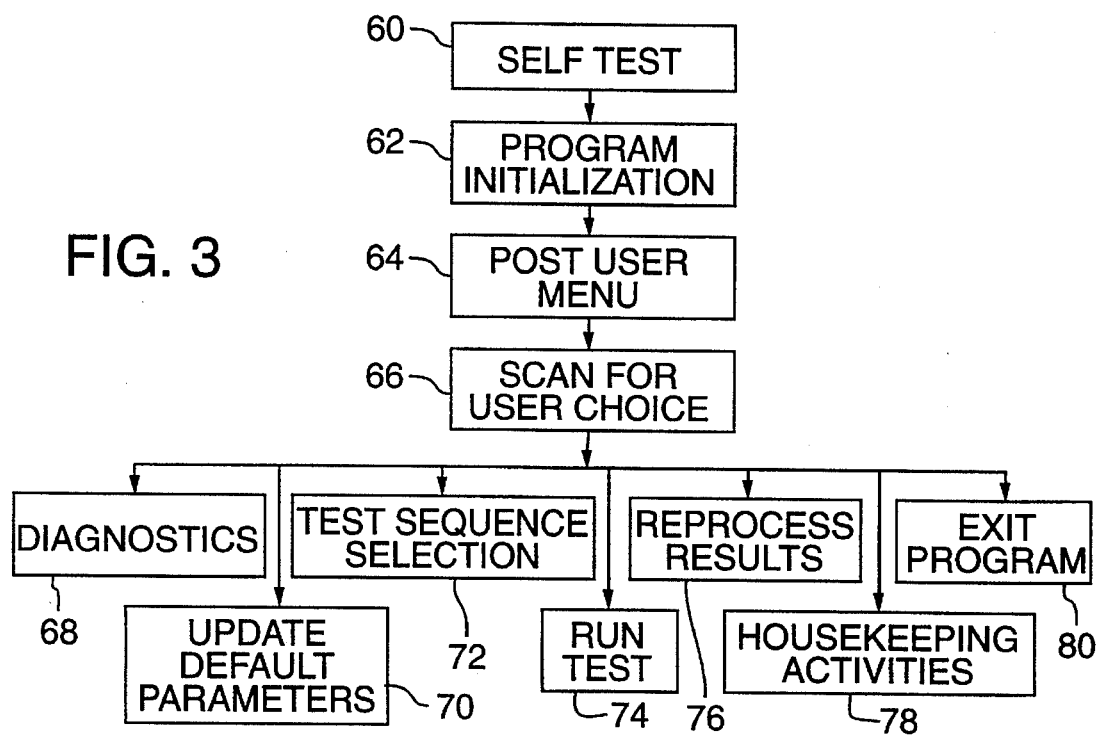
FIG. 3 is a flow diagram illustrating certain functions of software useful for practicing the invention.

FIG. 3 is a flow diagram that illustrates certain steps performed by the software which controls processor 12. First, method step 60 of FIG. 3 directs the processor 12 to perform a diagnostic test. In step 62, the program is initialized, and in step 64 a user menu is displayed. The operator has the option to select any of the possible choices listed on the user menu. In step 66, the processor is directed to scan for the selection entered by the operator.

The first possible selection by the operator is to run diagnostics, shown as step 68 of FIG. 3. The operator also has other possible selections, such as: step 70, which updates the default parameters; step 72, which tests the sequence selection; step 74, which directs the processor 12 to perform certain tests; step 76, which directs the processor 12 to reprocess the results obtained; step 78, which directs the processor 12 to perform certain housekeeping functions; and finally step 80, which is an exit program step.

Figure 4:
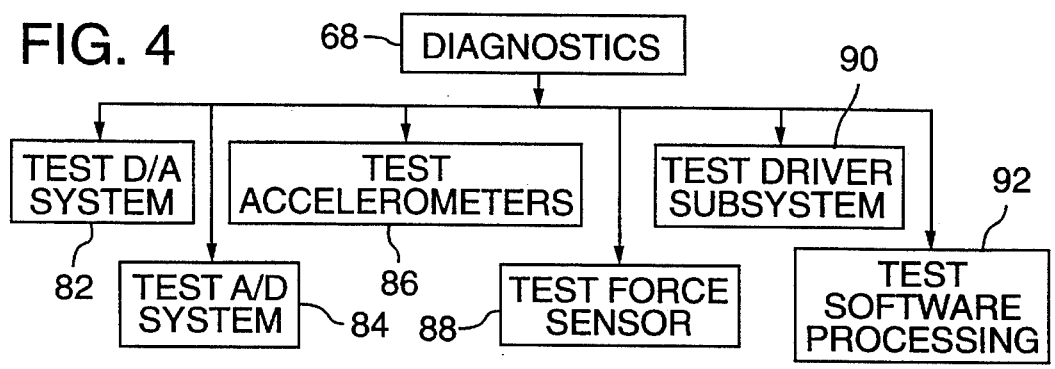
FIG. 4 is a flow diagram illustrating certain aspects of the diagnostic portion of the software illustrated in FIG. 3.

FIG. 4 illustrates certain menu functions associated with the diagnostic step 68. The diagnostic step allows the operator to verify that each portion of the apparatus 10 is functioning properly. The menu functions illustrated in FIG. 4 include: (1) step 82, testing the D/A analog system, such as D/A converter 36; (2) step 84, testing the A/D converter system, such as A/D converters 50, 52, 54 and 56; (3) step 86, testing the accelerometers, such as accelerometers 26, 28 and 30; (4) step 88, testing the force sensor 24; (5) step 90, testing the driver subsystem, such as that used with driver 22; and (6) step 92, testing the software processing.

F. CALCULATION OF MATERIAL STRENGTH AND QUALITY USING DIGITIZED DATA IN A NEURAL NETWORK MODEL

1. Transfer Function

Figure 5:
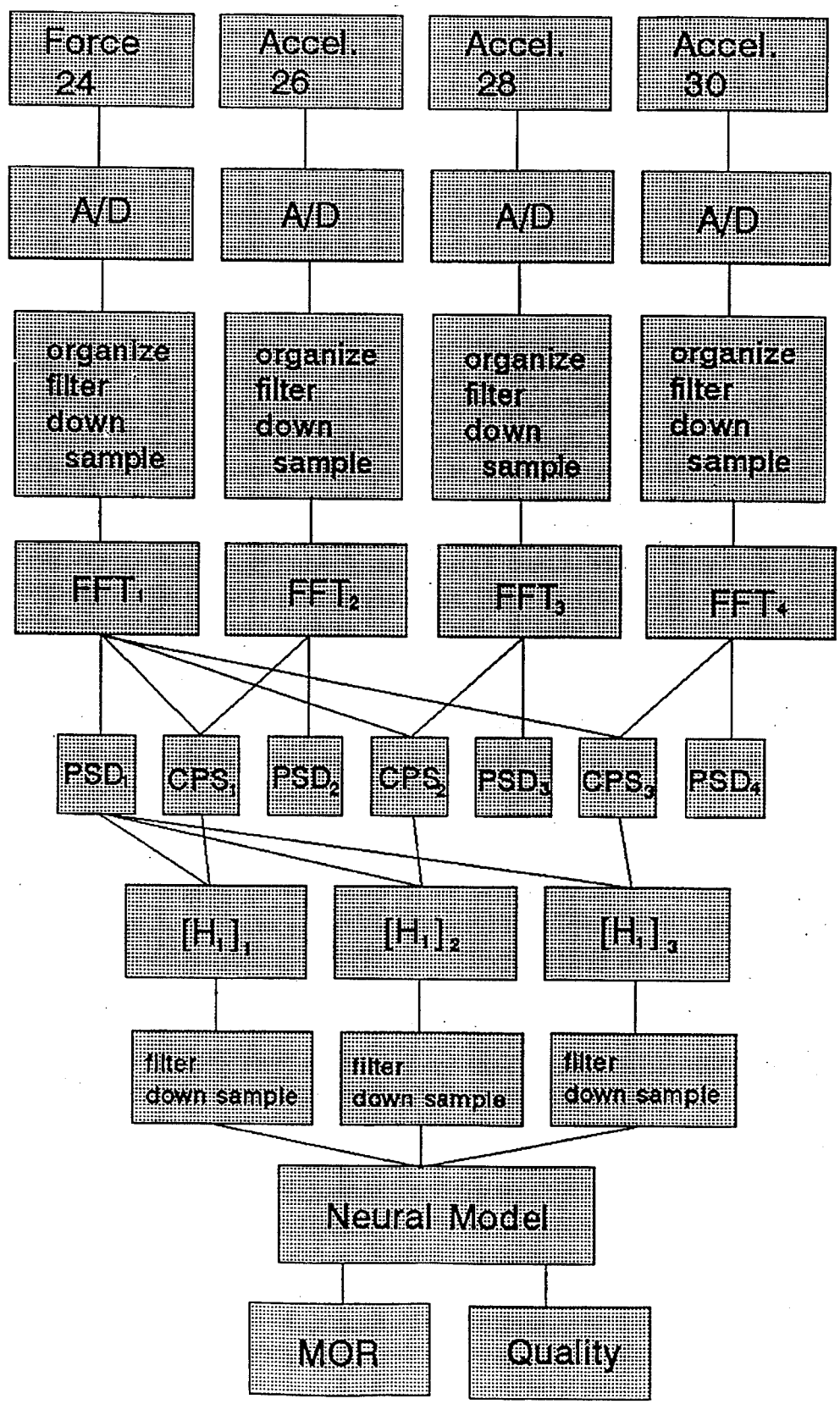
FIG. 5 is a schematic diagram illustrating certain software processes for data collection and analysis.

Certain features of collecting and analyzing data according to the present invention will now be described as illustrated schematically in FIG. 5. The analog signals from the force sensor 24 and accelerometers 26, 28 and 30 are sampled in parallel by the 16 bit sigma-delta analog-to-digital converters 36 at a per channel rate of 32 kHz. The digitized data is then organized, filtered and down-sampled by the digital-signal processors in realtime and then buffered into the personal computer for further data processing. The digital-signal processors examine the data stream for hardware and data errors, and are programmed to inform the main personal computer of any potential problems.

Thereafter, several processing steps are performed. First, all time series data can be saved to disk for long term storage. The waveforms are then converted to frequency domain arrays using a fast Fourier transform (FFT). This step can be performed by conventional code implementations, and therefore need not be discussed in more detail. The next step is to compute the power spectral densities (PSD) and the crosspower spectrums (CPS) from the FFT arrays. From these intermediate arrays, the desired input-output material transfer functions, shown as $H_1$ in FIG. 5, and the coherence (COH) are determined. The magnitude component of each transfer function is then computed. A confidence estimator is computed from the coherence to evaluate the initial quality of the analog signals. Next, each function $H_1$ is checked for aliasing caused by numeric scaling and roundoff errors. The magnitude component of $H_1$ is then low-pass filtered and down-sampled to produce the needed number of elements for the specific input required for the neural network model. The neural network software routines are then used to generate the prediction of material strength.

2. Neural Network Model

The digitized data of the transfer function is input to a set of linear equations that was derived using a neural network. Neural networks are commonly used in a variety of applications. There are a number of publications describing neural networks, including: (1) Baffes et al.'s *NETS, A Neural Network Development Tool*, NASA-COSMIC ID#MSC-22108 (1991); (2) Eberhart et al.'s *Neural Network PC Tools, a Practical Guide*, (Academic Press, Inc. 1990); (3) Gelb's *Applied Optimal Estimation*, (MIT press, 1980); (4) Rumelhart et al.'s *Parallel Distributed Processing*, (MIT Press, Vols. 1 and 2); and (5) Weiss et al.'s *Computer Systems that Learn*, (Morgan Kaufmann Publishers, Inc., 1991). Each of these references is incorporated herein by reference. The set of linear equations are used to predict pole strength in terms of MOR, as well as determining pole quality. The prediction equations from the neural model have the form:

$$C_k = \Sigma B_j s_{jk}$$

where $$B_j = \Sigma A_i r_{ij}$$

For these equations, $C_k$ is the predicted value which can be MOR or some quality index value. The predicted value is determined by multiplying the value of the hidden array $B_j$ of the neural network by a unique weighting parameter $S_{jk}$. Likewise, $B_j$ is determined by multiplying the input array $A_i$ of the neural network by another weighting parameter $r_{ij}$.

II. USING THE DEVICE AND METHOD

A prototype has been used to test wooden utility poles. More specifically, Southern pine, Douglas fir and cedar species utility poles have been tested. Moreover, comparison tests have been conducted to compare the performance of the present invention to certain commercially available methods and devices, including the PoleTest™, DE-K Tector®, I-section, and velocity test. A drill and bore analysis also was conducted. The tests were conducted as closely as possible to either the manufacturers specifications or accepted practices in the field.

Tests with the device of the present invention were conducted by coupling the device and plural accelerometers to the pole in accordance with the discussion provided above, and as illustrated schematically in FIG. 2. Data was then collected by testing approximately 160 utility poles.

The results of these tests are summarized below in TABLE 1. The results are presented in terms of $R^2$, which is a statistical measure of the accuracy of a statistical prediction. A prediction is perfect when $R^2$ is 1.0.

The PoleTest method referred to in Table 1 was developed by Engineering Data Management. The PoleTest method generates a sound wave in the test material by hitting the test material with an impact device, such as a pendulum-type tool. The PoleTest uses an undisclosed waveform analysis method to process the data from the accelerometers. This information, along with the diameter and species of the pole, is used to statistically predict the breaking strength of the pole at groundline through a correlation analysis. Tests of this equipment have showed a very poor predictive ability in determining the MOR of an in-service utility pole.

The DE-K Tector® is produced by Heath Energy Services, and is described in U.S. Pat. No. 3,531,983. The DE-K Tector® generates a sound wave in the test material by striking the material with an impact hammer. The DE-K Tector® also uses one accelerometer. An inspector hits one side of the test material while holding the receiving accelerometer on the opposite surface of the pole diameter. The DE-K Tector® examines the ratio of the amplitude of the high and low frequency components to predict whether the pole is good, questionable or bad. However, this device misidentifies poles as being either good or bad, and also may require repeat testing to provide an accurate assessment of the pole quality. It is important to note that the DE-K Tector® does not predict strength, but rather predicts whether the pole is good, or whether additional conventional tests need to evaluate the pole. The DE-K Tector® has a numeric scale output of ±25 which can be correlated with the breaking strength of the pole.

The I-section test referred to in Table 1 uses a bore and shell thickness gauge to determine the remaining sound wood in the pole. The I-section test calculates the section modulus (I) of the pole. This can then be used to determine the reduction of strength based on the reduction in the cross section of the pole.

TABLE 1

| COMPARISON OF INSPECTION DEVICES TO PREDICT MOR | |
|---|---|
| METHOD | $R^2$ |
| PoleTest | 0.17 |
| DE-K Tector ® | 0.15 |
| I-section | 0.36 |
| Present method | 0.77 (0.94)* |

*The neural model had an $R^2$ prediction of 0.94. However, when a test set of data that was not used to develop the model was analyzed by the method and apparatus of the present invention, the value, not unexpectedly, dropped to 0.77.

As shown in TABLE 1, the present invention is much more accurate in predicting strength than the known methods. The $R^2$ value using the present method is at least twice as good as known devices. The present method has an $R^2$ value which is at least 4.5 times better than the PoleTest and DE-K Tector® method. The best prior technique that has been tested is the I-section method. However, the present method has an $R^2$ value which is at least twice as good as the value obtained with the I-section method.

In summary, the present invention provides a method of testing for remaining strength, particularly wooden articles such as utility poles, which is significantly superior to previously developed testing devices and/or methods.

The present invention has been described in accordance with preferred embodiments. However, it will be understood that certain substitutions and alterations may be made thereto without departing from the spirit and scope of the following claims.

We claim:

1. An apparatus for evaluating material strengths, comprising:

a frequency sweeping waveform generator that generates a sinusoidal waveform and sweeps frequencies between a low frequency and a high frequency while evaluating material strengths, wherein the low frequency is from about 10 Hz to about 150 Hz, and the high frequency is from about 6,000 Hz to about 24,000 Hz;

a driver that receives signals from the generator and which is coupled to an elongated material at a drive point for transmitting the frequency sweeping waveform to the material;

a force sensor that is coupled to the material at or adjacent to the drive point for measuring force transmitted into the material as the waveform sweeps between the low and the high frequencies;

a first accelerometer that is coupled to the material at or adjacent to the drive point for measuring response of the material to the transmitted waveform as the waveform sweeps between the low and the high frequencies; and a microprocessor that receives signals from the force sensor and accelerometer and evaluates material strength based on the signals from the force sensor and accelerometer as the waveform sweeps between the low and the high frequencies.

2. The apparatus according to claim 1 and further including a second accelerometer that is coupled to the material at a point substantially diametrically opposed to the drive point, wherein the second accelerometer transmits signals to the microprocessor.

3. The apparatus according to claim 2 and further including a third accelerometer that is spaced from the drive point, wherein the third accelerometer transmits signals to the microprocessor.

4. The apparatus according to claim 3 wherein the third accelerometer is spaced from the drive point by a distance that is less than about 24 inches.

5. The apparatus according to claim 1 wherein the waveform generator generates frequencies of from about 150 Hz to about 6,000 Hz.

6. The apparatus according to claim 1 wherein the material is a wooden article.

7. The apparatus according to claim 6 wherein the wooden article is a utility pole.

8. The apparatus according to claim 7 wherein the drive point is at or near groundline.

9. The apparatus according to claim 1 wherein the driver is an electromechanical driver.

10. The apparatus according to claim 1 wherein the driver is a piezo-ceramic driver.

11. The apparatus according to claim 1 wherein the driver is an electromagnetic/piezo-ceramic driver.

12. The apparatus according to claim 1 wherein the device is manually transportable.

13. An apparatus for the nondestructive evaluation of strength remaining in a wooden article, comprising:

a frequency sweeping waveform generator that generates a sinusoidal waveform and which sweeps frequencies between a low frequency and a high frequency while evaluating the strength of a material, wherein the low frequency is from about 10 Hz to about 150 Hz, and the high frequency is from 6,000 Hz to about 24,000 Hz;

a driver for transmitting the frequency sweeping waveform into an elongated wooden article, the driver being electronically coupled to the waveform generator and coupled to the wooden article at a drive point;

a force sensor that is coupled to the elongated wooden article at or adjacent to the drive point for measuring force transmitted into the wooden article as the waveform sweeps between the low and the high frequencies;

a first accelerometer that is coupled to the material at or substantially adjacent to the drive point for measuring response of the wooden article to the transmitted waveform as the waveform sweep between the low frequency and the high frequency;

a second accelerometer that is coupled to the article at a point that is substantially diametrically opposed to the drive point for measuring response of the wooden article to the transmitted waveform as the waveform sweeps between the low frequency and the high frequency; and a microprocessor that receives signals from the sensor and accelerometers and evaluates material strength based on the signals from the force sensor and the accelerometers as the waveform sweeps between the low and the high frequencies.

14. The apparatus according to claim 13 and further including a third accelerometer that is coupled to the wooden article at a point spaced from the drive point.

15. The apparatus according to claim 14 wherein the third accelerometer is spaced from the drive point by a distance that is less than about 24 inches.

16. The apparatus according to claim 13 wherein the wooden article is an in-service utility pole.

17. The apparatus according to claim 16 wherein the drive point is at or near groundline.

18. The apparatus according to claim 13 wherein the driver is selected from the group of drivers consisting of electromechanical drivers, piezo-ceramic drivers and electromagnetic/piezo-ceramic drivers.

19. A manually transportable apparatus for the nondestructive evaluation of material strength remaining in in-service utility poles, the apparatus comprising:

a waveform generator that comprises either (1) a sinusoidal frequency sweeping waveform generator that sweeps frequencies between a low frequency and a high frequency while evaluating material strength remaining in a utility pole, wherein the low frequency is from about 10 Hz to about 150 Hz, and the high frequency is from about 6,000 Hz to about 24,000 Hz or (2) a pseudo random waveform generator that continuously generates a waveform within the frequency range of from about 150 Hz to about 6,000 Hz during evaluation of material strength remaining in a utility pole;

a driver for transmitting the waveform into the utility pole, the driver being electronically linked to the waveform generator and mechanically coupled to the pole at a drive point;

a force sensor that is mechanically coupled to the driver and to the pole at or adjacent to the drive point for measuring force transmitted into the pole as the sinusoidal waveform generator sweeps frequencies between the low and the high frequencies or the pseudo random waveform generator generates a waveform within the frequency range;

a first accelerometer that is coupled to the pole at or adjacent to the drive point for continuously measuring response of the pole to the (1) waveforms of frequencies sweeping between the low frequency and the high frequency that are transmitted to the pole by the driver, or (2) a waveform within the range of from about 150 Hz to about 6,000 Hz, that is transmitted to the pole by the driver; and a microprocessor that receives signals from the sensor and accelerometer and evaluates strength of the pole based on the signals from the force sensor and the accelerometer as (1) the sinusoidal waveform generator sweeps frequencies between the low and the high frequencies, or (2) the pseudo random waveform generator generates a waveform within the frequency range.

20. The apparatus according to claim 19 and further including a second accelerometer that is coupled to the pole at a point substantially diametrically opposed to the drive point.

21. The apparatus according to claim 20 and further including a third accelerometer that is mechanically coupled to the pole at a point spaced from the drive point.

22. The apparatus according to claim 21 wherein the third accelerometer is spaced from the drive point by a distance that is less than about 24 inches.

23. The apparatus according to claim 19 wherein the drive point is at or near groundline.

24. A method for testing the strength of a material, comprising:

coupling a force sensor and a first accelerometer to a material;

transmitting into the material at a drive point, while testing the strength of the material, either (1) a sinusoidal waveform having a frequency that, during a testing operation, continuously sweeps between a low frequency and a high frequency, wherein the low frequency is from about 10 Hz to about 150 Hz and the high frequency is from about 6,000 Hz to about 24,000, or (2) a pseudo random waveform within the frequency range of from about 150 Hz to about 6,000 Hz;

measuring force transmitted into the material at a point at or substantially adjacent to the drive point using the force sensor;

measuring response to the transmitted waveform by the material using the first accelerometer as (1) the frequency sweeps between the low frequency and the high frequency, or (2) the pseudo random waveform is transmitted to the material; and evaluating strength remaining in the material based on the signals from the force sensor and the first accelerometer as (1) the frequency sweeps between the low and the high frequencies, or (2) the pseudo random waveform is transmitted to the material within the frequency range.

25. The method, according to claim 24 wherein the first accelerometer is coupled to the material at or substantially adjacent to the drive point.

26. The method according to claim 24 wherein the step of measuring the response to the transmitted waveform by the material further comprises mechanically coupling a second accelerometer to the material at a point that is substantially diametrically opposed to the drive point.

27. The method according to claim 24 wherein the frequency range of the sinusoidal waveform is from about 150 Hz to about 6,000 Hz.

28. The method according to claim 24 wherein the step of transmitting comprises transmitting the waveform into the material a plurality of times.

29. The method according to claim 24 wherein the waveform has a frequency sweep time of less than about 2 seconds.

30. A nondestructive method for testing the strength remaining in a utility pole, the method comprising:

coupling a force sensor to the pole at or adjacent to a drive point;

coupling a first accelerometer to the pole at or adjacent to the drive point;

coupling at least a second accelerometer to the pole at a position that is substantially diametrically opposed to the drive point;

transmitting into a utility pole at the drive point either (1) a sinusoidal waveform having a frequency that can sweep from a low frequency to a high frequency, wherein the low frequency is from about 10 Hz to about 150 Hz and the high frequency is from about 6,000 Hz to about 24,000, or (2) a pseudo random waveform within the frequency range of from about 150 Hz to about 6,000 Hz; and inputting digitized outputs from the force sensor and accelerometers into a neural network model to determine the strength remaining in the pole.

31. The method according to claim 30 wherein the sinusoidal waveform frequency range is from about 150 Hz to about 6,000 Hz.

* * * * *